(12) United States Patent
Haddock et al.

(10) Patent No.: US 10,952,744 B2
(45) Date of Patent: Mar. 23, 2021

(54) FEMORAL NOTCH PREPARATION GUIDE

(71) Applicant: Smith & Nephew, Inc., Memphis, TN (US)

(72) Inventors: Sean M. Haddock, Germantown, TN (US); Michael Jackson, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 210 days.

(21) Appl. No.: 16/197,559

(22) Filed: Nov. 21, 2018

(65) Prior Publication Data

US 2019/0150948 A1 May 23, 2019

Related U.S. Application Data

(60) Provisional application No. 62/589,107, filed on Nov. 21, 2017.

(51) Int. Cl.
| | |
|---|---|
| *A61B 17/15* | (2006.01) |
| *A61F 2/46* | (2006.01) |
| *A61B 17/17* | (2006.01) |
| *A61F 2/38* | (2006.01) |
| *A61B 17/16* | (2006.01) |

(52) U.S. Cl.
CPC ........ *A61B 17/155* (2013.01); *A61B 17/1764* (2013.01); *A61F 2/4684* (2013.01); *A61B 17/1604* (2013.01); *A61B 17/1675* (2013.01); *A61F 2/3859* (2013.01)

(58) Field of Classification Search
CPC .......................... A61B 17/155; A61B 17/1764
See application file for complete search history.

(56) References Cited

U.S. PATENT DOCUMENTS

| | | | |
|---|---|---|---|
| 8,551,101 B2 * | 10/2013 | Kuczynski | ......... A61B 17/1604 606/88 |
| 8,771,280 B2 | 7/2014 | Bailey et al. | |
| 8,911,444 B2 * | 12/2014 | Bailey | .................... A61B 17/15 606/87 |
| 9,011,453 B2 | 4/2015 | Parisi et al. | |
| 9,119,734 B2 | 9/2015 | Dees | |

\* cited by examiner

*Primary Examiner* — Andrew Yang
(74) *Attorney, Agent, or Firm* — Kacvinsky Daisak Bluni PLLC

(57) ABSTRACT

A notch preparation guide for engagement with a femoral trial component according to some embodiments includes an anterior portion having an anterior slot arranged to receive a portion of a first cutting instrument therein, and a posterior portion having a posterior slot arranged to receive a portion of a second cutting instrument therein. The anterior slot and the posterior slot are arranged to capture a portion of a distal femur there between for removal by either the first cutting instrument or the second cutting instrument. In some embodiments, the first cutting instrument is a saw and the second cutting instrument is a chisel. In some embodiments, the notch preparation guide includes a lock adapted to move between an open position wherein the notch preparation guide is detachable from the femoral trial component and a closed position wherein the notch preparation guide is fixedly attached to the femoral trial component.

29 Claims, 13 Drawing Sheets

FEMORAL NOTCH PREPARATION GUIDE

CROSS-REFERENCE TO RELATED APPLICATIONS

The present application claims the benefit of U.S. Provisional Patent Application No. 62/589,107, filed on 21 Nov. 2017, the contents of which are incorporated by reference in their entirety.

TECHNICAL FIELD

The present disclosure generally relates to surgical orthopedic trials and methods, and more particularly but not exclusively relates to such a system that can be used to guide preparatory cuts that assist in preparation of a femur bone for implantation of a final implant.

BACKGROUND

Trial components are commonly used during joint replacement surgery to test the fit and alignment of an implant relative to a bone that was reshaped by a surgeon. The use of trial components is beneficial as it avoids damage to the actual implants during testing of the trial components.

Total knee arthroplasty (TKA) surgeries generally involve a surgeon affixing a femoral component to a patient's femur and a tibial component to the patient's tibia. The femoral component is placed on the patient's distal femur after appropriate resection, and the tibial component is placed on the patient's tibial plateau after appropriate preparation. Adjustments to the cuts on either the tibial or femoral surfaces and different component sizes are considered during the surgery. Moreover, the knee is flexed and extended to determine the proper size, fit, and adjustment for the components.

Accurately positioning and fitting the trial components to respective portions of the joint enables the surgeon to test the fit and performance of the components both statically and dynamically throughout a desired range of motion without introducing the actual prosthetic implant into the patient. This is important for many reasons. First, each patient has a different bone structure and geometry. Motion of the tibia relative to the femur about every axis varies from one patient to the next. Some knee replacement patients may have functionality problems with medial/lateral, anterior/posterior, or varus/valgus ligaments, and an implant that constrains the movement of the knee joint may be needed to enhance stability. In these instances, the surgeon may need to use a femoral implant with a constrained box geometry to ensure stability of the knee once the ligaments have been released.

Many systems for such a cruciate ligament sacrificing procedure use a constraining box geometry cutting block/guide and a separate femoral trial in order to prepare the bone to receive a permanent implant and then test the fit. In this process, the surgeon makes the initial cut(s) using a cutting block that is placed on the femur. Such cutting blocks are typically square (i.e., they are not shaped like the actual implant) and may be secured in place on the resected femur. Anterior and posterior chamfer resections are then made to shape the bone to receive the inner portion (i.e., the "box portion") of the femoral component. Femoral box resection cuts then need to be made. Typically, a separate femoral box cutting guide is secured on the surface of the femoral bone, and a reciprocating saw and/or box chisel is used to remove medial, lateral, and proximal (and anterior in some instances) portions of bone in the notch. Then, for trial reduction, the cutting guide is removed and a femoral trial component with box geometry built-in to the component is secured on the prepared femur. A tibial tray is placed on the prepared tibia and if necessary, a trial patellar component is also selected. Once the components are in place, the surgeon checks the range of motion and stability of the knee.

Femoral components typically have inner intersecting flat surfaces that interface with a surgically prepared distal femoral surface, and an outer surface with a curvature that faces the corresponding tibial component attached to the patient's tibial post. A different amount of bone depth may need to be removed, depending upon the patient and the type of femoral implant that will be used. There are many different types of instruments that are used to prepare the distal femur, including cutting blocks, reamers, saws, chisels, and trial components.

One technique of finishing or removing a portion of the distal femur includes a freehand saw cut. Once resections are completed, the femoral trial component can be placed on the distal femur. Once the femoral trial component is positioned on and secured to the distal femur, the surgeon will use a saw or other cutting instrument against one edge of the femoral trial component as a guide to remove bone within the trochlear groove.

One example of such technique includes U.S. Pat. No. 9,119,734 that provides a femoral trial component that can be used as a guide for the box cut. The trial component includes an opening between condylar components wherein the opening provides an access area through which instruments may pass in order to prepare box geometry cuts in the femur. The trial component includes tracks that can be used to guide box cutting guides, chisels, and/or reamers. However, many surgeons have difficulty with this step to form a precise cut on the bone. Moreover, many surgeons often forget to perform this step. If the bone is not properly prepared, the femur implant will not properly attach to the distal femur and the femur implant will not function correctly.

For these reasons among others, a need remains for further improvements in this technological field.

SUMMARY

In one embodiment, a notch preparation guide for engagement with a femoral trial component includes an anterior portion having an anterior slot arranged to receive a portion of a first cutting instrument therein, a posterior portion having a posterior slot arranged to receive a portion of a second cutting instrument therein, wherein the anterior slot and the posterior slot are arranged to capture a portion of a distal femur there between for removal by either the first cutting instrument or the second cutting instrument. In some embodiments, the first cutting instrument is a saw and the second cutting instrument is a chisel. In some embodiments, the notch preparation guide includes a lock adapted to move between an open position wherein the notch preparation guide is detachable from the femoral trial component and a closed position wherein the notch preparation guide is fixedly attached to the femoral trial component. Further embodiments, forms, features, and aspects of the present application shall become apparent from the description and figures provided herewith.

BRIEF DESCRIPTION OF THE FIGURES

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION OF ILLUSTRATIVE EMBODIMENTS

Figure 1:
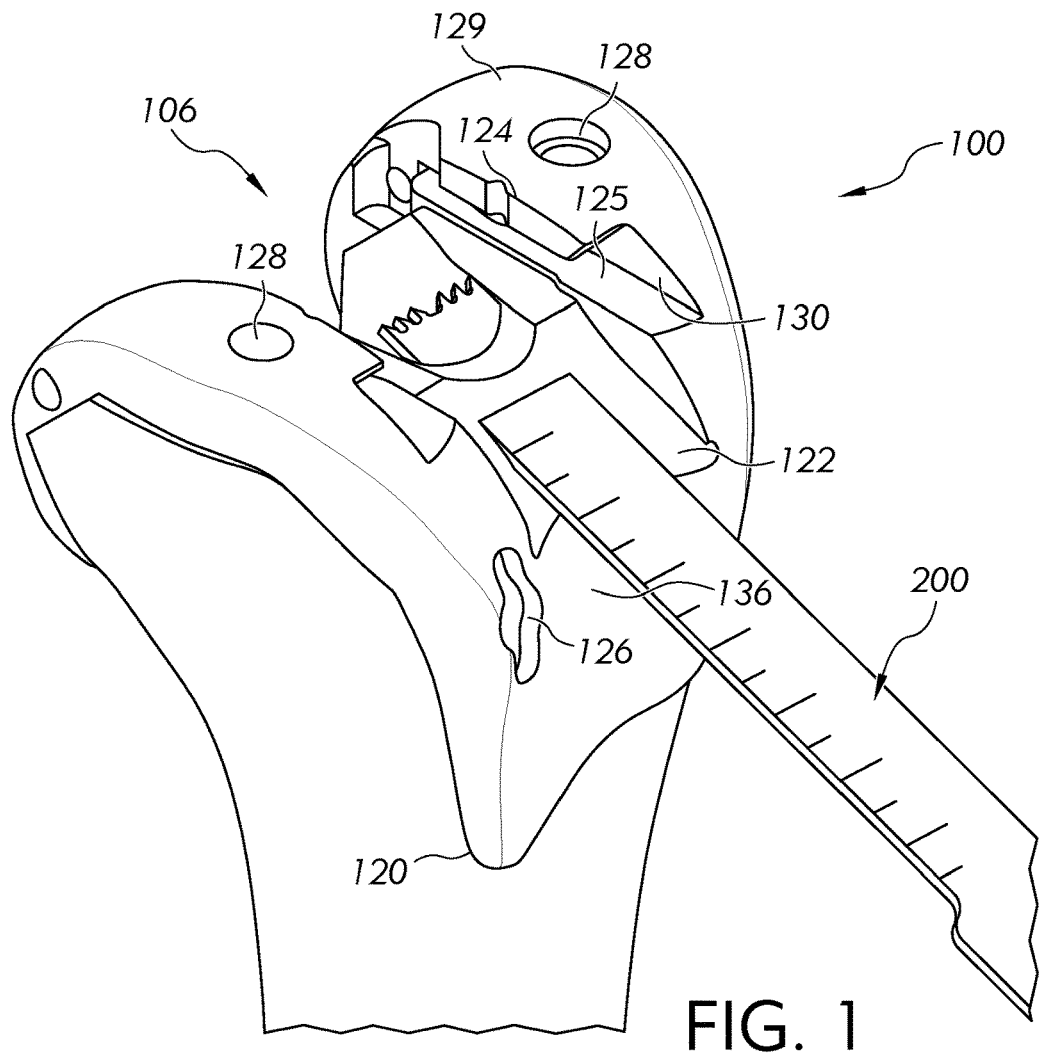
FIG. 1 is a perspective view of a trial femoral component implanted on a femur and a saw.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Although such phrases are not necessarily referring to the same embodiment, it should be appreciated that some embodiments may include features not specifically described as being included in the same embodiment unless stated to the contrary. For example, the statements that "in some embodiments, an apparatus may include a first component" and "in some embodiments, the apparatus may include a second component" should be interpreted to include embodiments in which the apparatus includes both the first component and the second component unless stated to the contrary or otherwise inconsistent with the description. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

In the drawings, some structural or method features may be shown in certain specific arrangements and/or orderings. However, it should be appreciated that such specific arrangements and/or orderings may not necessarily be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As shown in FIG. 1, there is provided an illustrative femoral trial component 100 and a saw blade 200. These components may be made out of any material that is appropriate for trialing purposes, for example metals such as zirconium, cobalt-chrome, stainless steel, titanium, or even polyethylene or other types of strong plastics or composites, such as graphites and polymers. The femoral trial component 100 has a J-shaped cross section, with the upper part of the "J" forming the anterior portion 120 and the hooks of the "J" forming the condyles or condylar components 108 of the trial component 100 with an articulating surface 136. This is perhaps shown more clearly in the perspective view of FIG. 5. The femoral trial component 100 may also have a stem portion, which can be a protrusion with an opening to receive a stem (not shown) that is received in a patient's intramedullary canal in order to secure component 100 in place. This allows trial component 100 to be trialed with various types of stems, such as offset stems, angled stems, and stems of various lengths and diameters.

The trial component 100 can include various resection slots along the anterior portion 120 and/or the condyles 108. During surgery, the surgeon may make various resections of the femur as needed, and the surgeon may use slots on trial component 100 to guide those resection cuts. The trial component 100 includes an opening 106, which is provided between condylar components 108.

Figure 3:
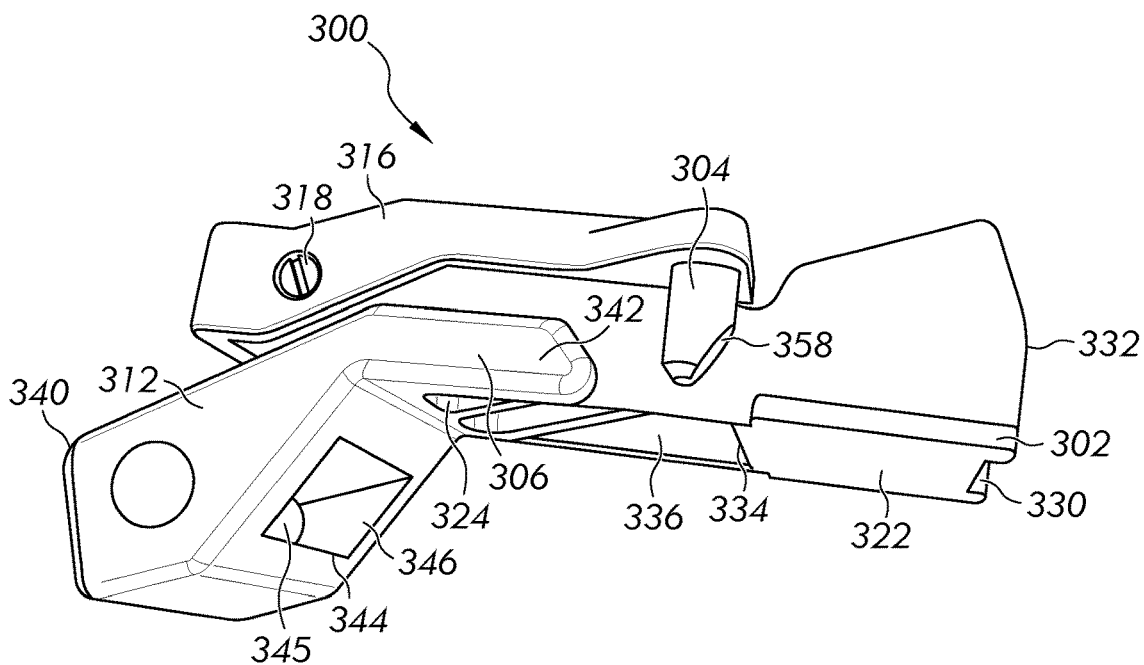
FIG. 3 is a side perspective view of the notch preparation guide illustrated in FIG. 2.
Figure 5:
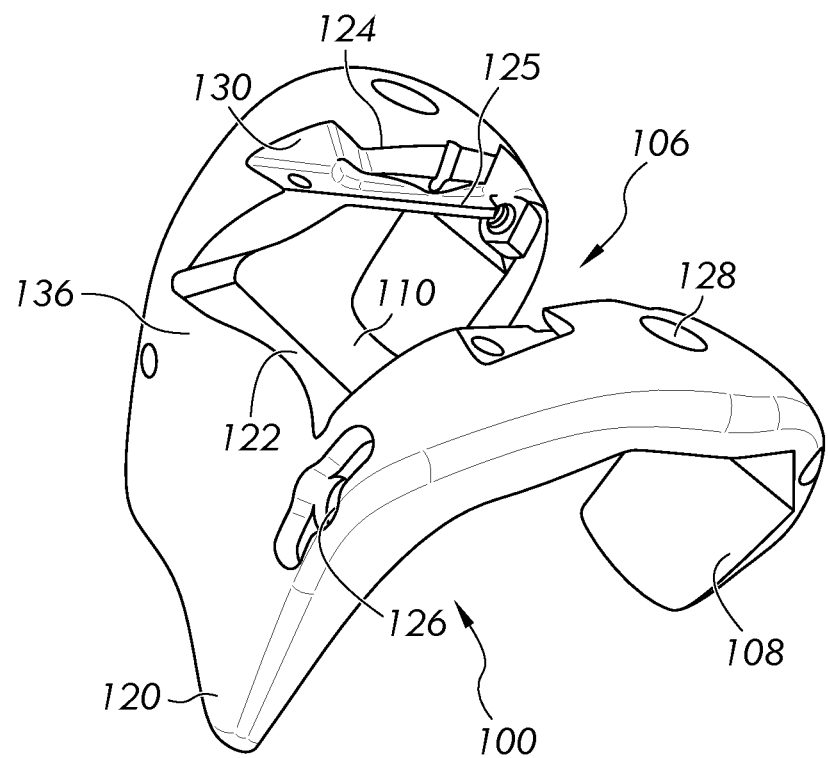
FIG. 5 is a perspective view of a trial femoral component according to one embodiment.

As illustrated in FIG. 5, the opening 106 defines a central portion 110 of the femoral trial component 100 that has an anterior-most portion 122 and opening side edges 124. In the particular embodiment shown in FIGS. 1 and 5, the opening side edges 124 define orientation slots 125. As described in further detail below, the orientation slots 125 are adapted to receive a notch preparation guide 300 as illustrated in FIG. 3. In the particular embodiment shown, the notch preparation guide 300 includes a pair of outer flanges 302. Edges of the outer flanges 302 may slide into orientation slots 125 to aid in securing the trial component 100 and notch preparation guide 300 together. The opening side edges 124 also include grooves 130 adapted to receive the notch preparation guide 300. In the particular embodiment shown, the notch preparation guide 300 includes a pair of legs 306. The legs 306 may slide into the grooves 130 to aid in securing the trial component 100 and notch preparation guide 300 together.

The femoral trial component 100 also features one or more fixation holes 126. Fixation holes 126 are adapted to receive pins, screws, pegs, or another securing mechanism to secure trial component 100 in place on the patient's bone during surgery. In certain embodiments, the fixation holes 126 may be used as drill guides.

The femoral trial component 100 includes a pair of receiving portions 128 on a distal surface 129, wherein the receiving portions 128 are adapted to receive pegs 304 of the notch preparation guide 300. The pegs 304 are intended to secure notch preparation guide 300 in place as explained in more detail below. The receiving portions 128 may or may not feature threads.

Figure 2:
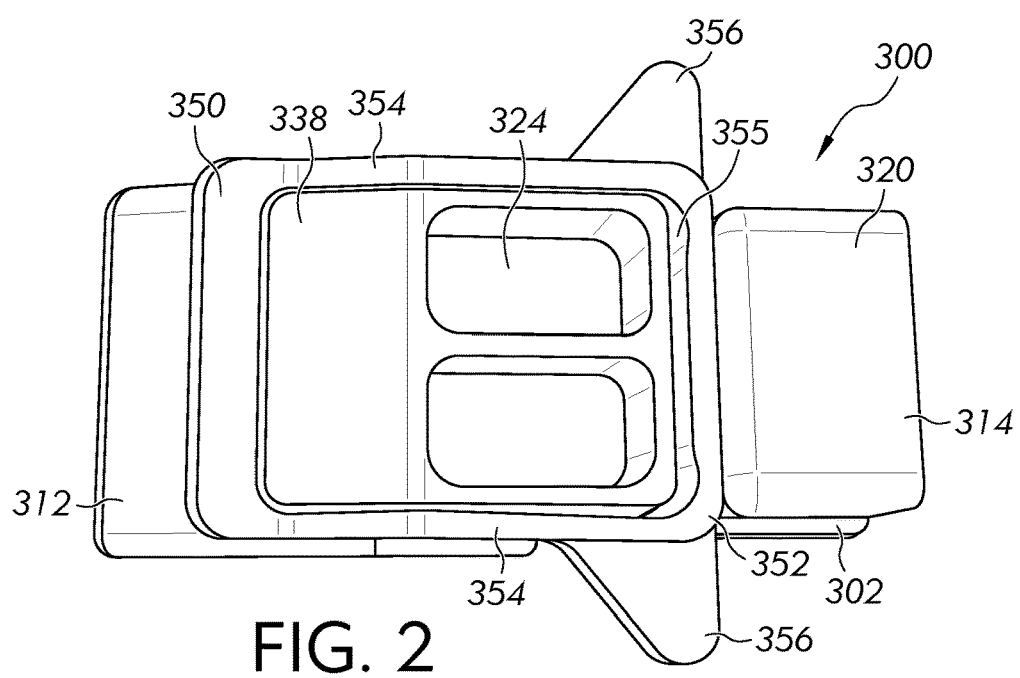
FIG. 2 is a top view of a notch preparation guide according to one embodiment.
Figure 4:
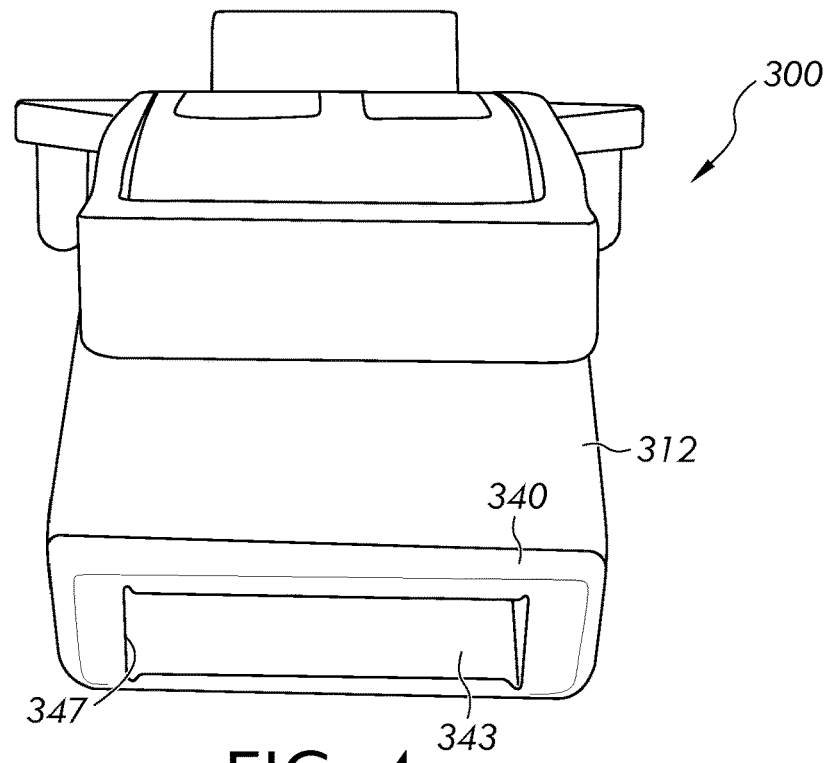
FIG. 4 is an anterior side view of the notch preparation guide illustrated in FIG. 2.

With reference to FIGS. 2, 3, and 4, the notch preparation guide 300 will be described in more detail. The notch preparation guide 300 includes an anterior portion 312 attached to a posterior portion 314. Optionally the anterior portion 312 and the posterior portion 314 can be monolithic or one-piece. In the illustrated embodiment, the notch preparation guide 300 includes a movable arm 316 pivotally attached to the posterior portion 314 at a pivot or hinge 318.

The notch preparation guide 300 includes a distal surface 320 opposite a proximal surface 322. The posterior portion 314 may include one or more openings or windows 324 that span between the distal surface 320 and the proximal surface 322. The windows 324 can be configured for viewing the portion of the bone to be removed during a surgical procedure or for additional access to the bone. In some embodiments, the posterior portion 314 does not include the windows 324. The posterior portion 314 spans between a posterior end 332 and an opposite anterior end 338. The posterior portion 314 includes a pair of outer flanges 302, wherein edges of the outer flanges 302 may slide into the orientation slots 125 to secure trial component 100 and notch preparation guide 300 together as described in more detail below.

Figure 7A:
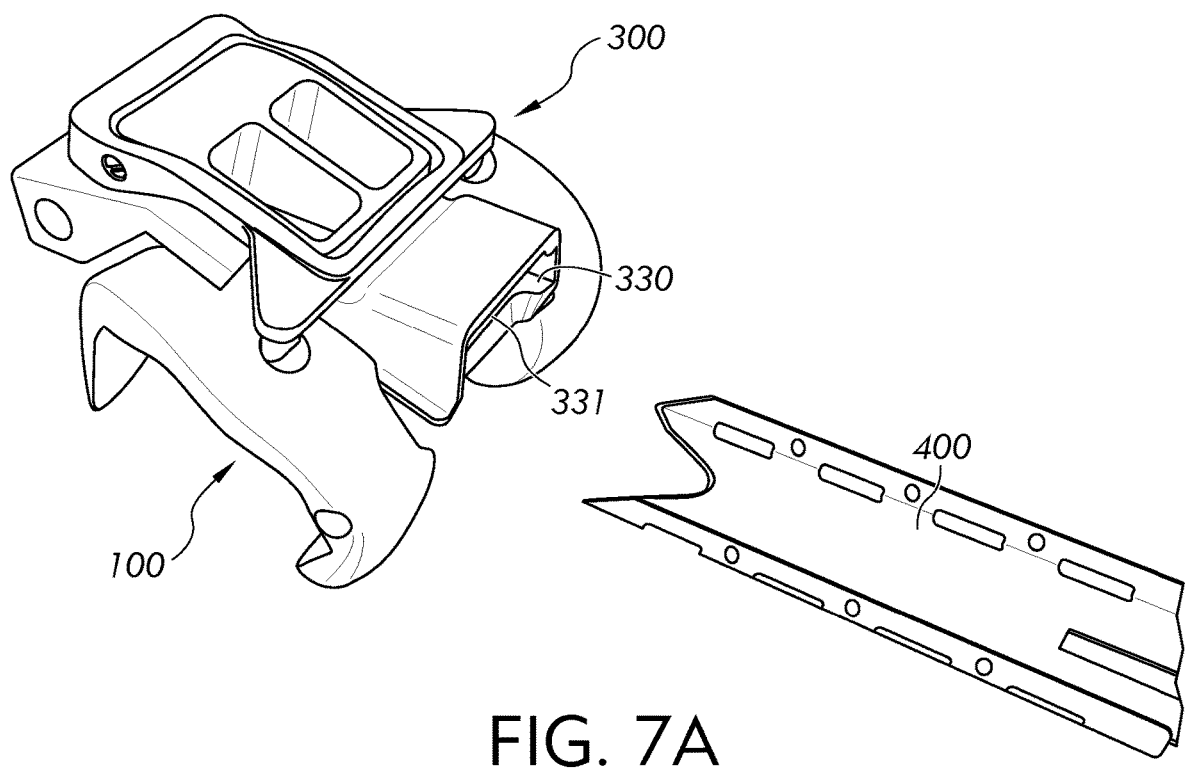
FIGS. 7A and 7B illustrate a posterior perspective view of the notch preparation guide illustrated in FIG. 2 and the trial femoral component illustrated in FIG. 5 with a chisel.
Figure 7B:
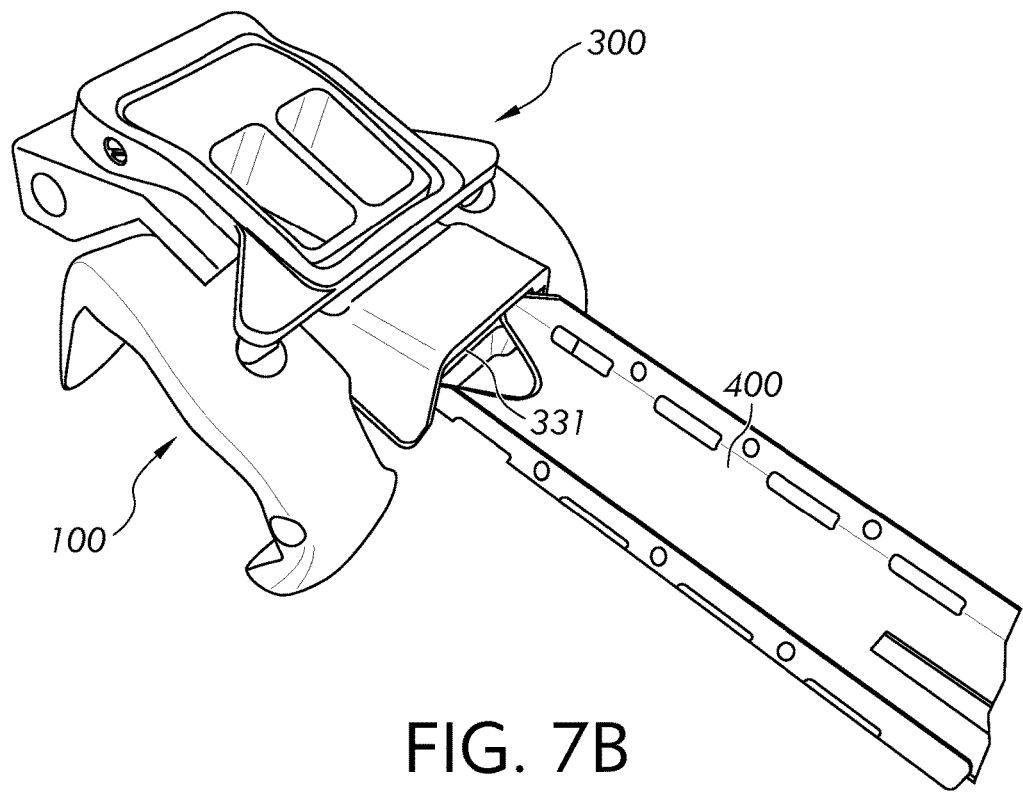

The posterior portion 314 includes a posterior slot 330 sized to receive a cutting instrument in the form of a chisel 400 as illustrated in FIGS. 3 and 7A. The chisel 400 includes a chisel blade 402 attached to a chisel handle 404. The chisel blade 402 has a U-shaped cross-section with a wide flat edge on the bottom and shorter flat sidewalls. The chisel 400 may be a single piece reusable type chisel or osteotome, or a chisel that includes an impact handle and a disposable chisel blade. The posterior slot 330 spans from an opening 331 at the posterior end 332 to an opening 336 at an interior edge 334. The posterior slot 330 is a captured guideway for the chisel 400 such that the chisel 400 fits through the opening 331, the posterior slot 330, and the opening 336, wherein the chisel 400 may be moved relative to the posterior slot 330. In one form, the posterior slot 330 is substantially rectangular in cross-sectional shape to correspond with the cross-sectional shape of the chisel 400, and forms a guideway for the chisel 400 to slide along. The posterior slot 330 can have a different cross-sectional shape as desired to receive the chisel 400 or other cutting instrument and facilitate movement of the chisel 400 or cutting instrument relative to the posterior slot 330.

The posterior portion 314 also includes an opening 336 adjacent the interior edge 334, wherein the opening 336 is configured to receive a portion of bone from the patient and the chisel 400. The chisel 400 may engage the portion of bone through the opening 336 after traveling through the posterior slot 330 during surgery. As discussed in further detail below, the anterior portion 312 includes an opening 346 that is configured to receive a portion of the chisel 400. The anterior portion 312 has an anterior slot 343 with an internal feature 345 therein such that the internal feature 345 is configured to engage the chisel 400 and stop the chisel 400 from further movement in the anterior slot 343.

The anterior end 338 of the posterior portion 314 includes a hinge 318 for attachment of the posterior portion 314 with the movable arm 316. The anterior end 338 of the posterior portion 314 is also fixedly attached to the anterior portion 312. In certain embodiments, the posterior portion 314 and the anterior portion 312 are one-piece or monolithic.

The anterior portion 312 spans between an anterior end 340 and a posterior end 342. The anterior portion 312 includes an anterior slot 343 sized to receive the saw 200 or another cutting instrument, and the anterior slot 343 spans from an opening 347 at the anterior end 340 to an opening 346 at an interior edge 344. The anterior slot 343 is a captured guideway for the saw 200 such that the saw 200 fits within and slides relative to the anterior slot 343. In one form, the anterior slot 343 is substantially rectangular in cross-sectional shape to correspond with the cross-sectional shape of the saw 200 and form a guideway for the saw 200. The anterior slot 343 can have a different cross-sectional shape as desired to receive the saw 200 or other cutting instrument.

Figure 8A:
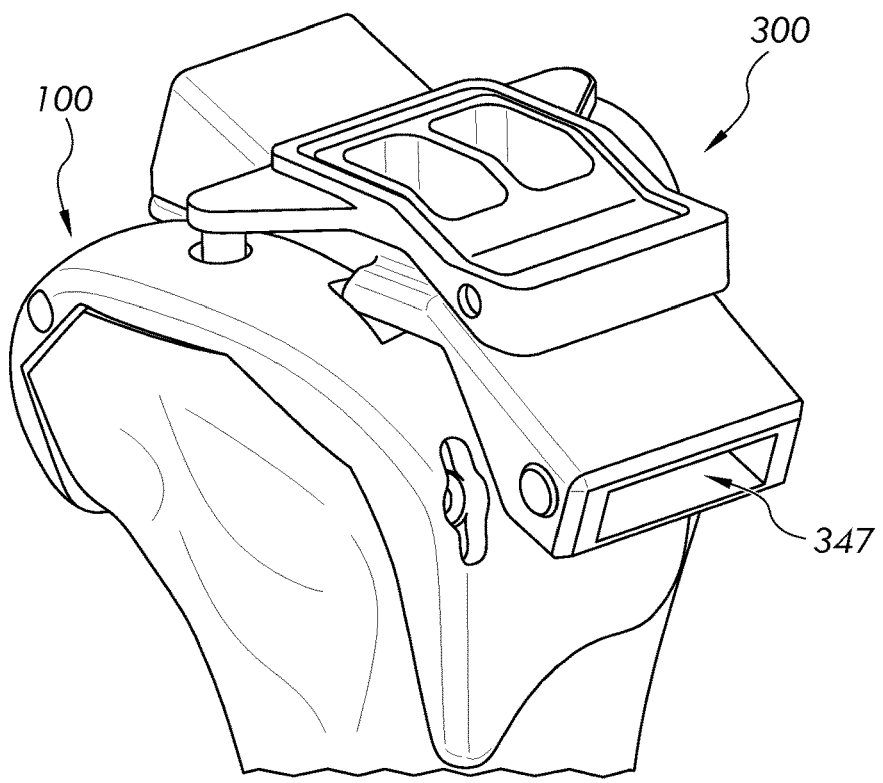
FIG. 8A is a perspective view of the notch preparation guide illustrated in FIG. 2 attached to the trial femoral component of FIG. 5 implanted on a femur.
Figure 8B:
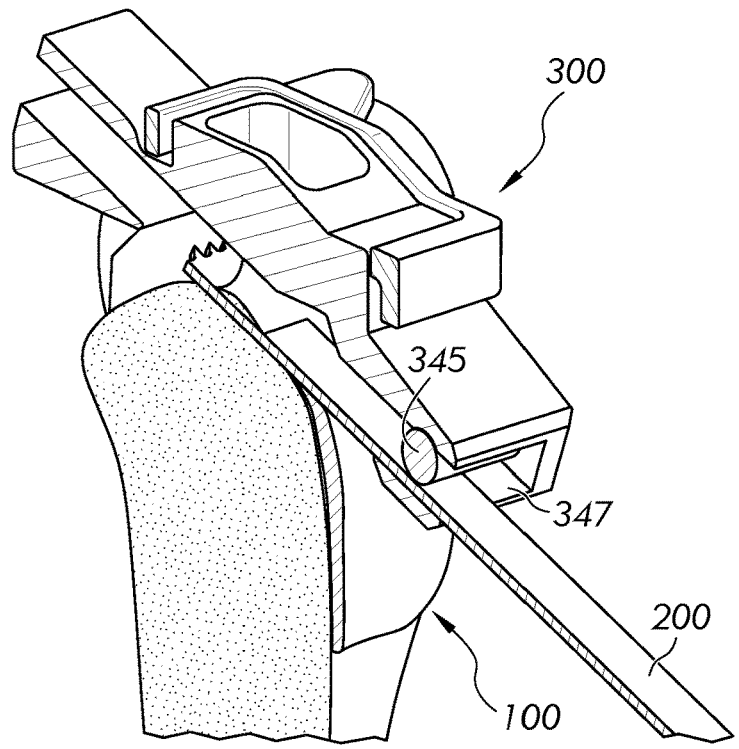
FIG. 8B is a cross sectional view of the notch preparation guide attached to the trial femoral component of FIG. 8A with a saw.
Figure 8C:
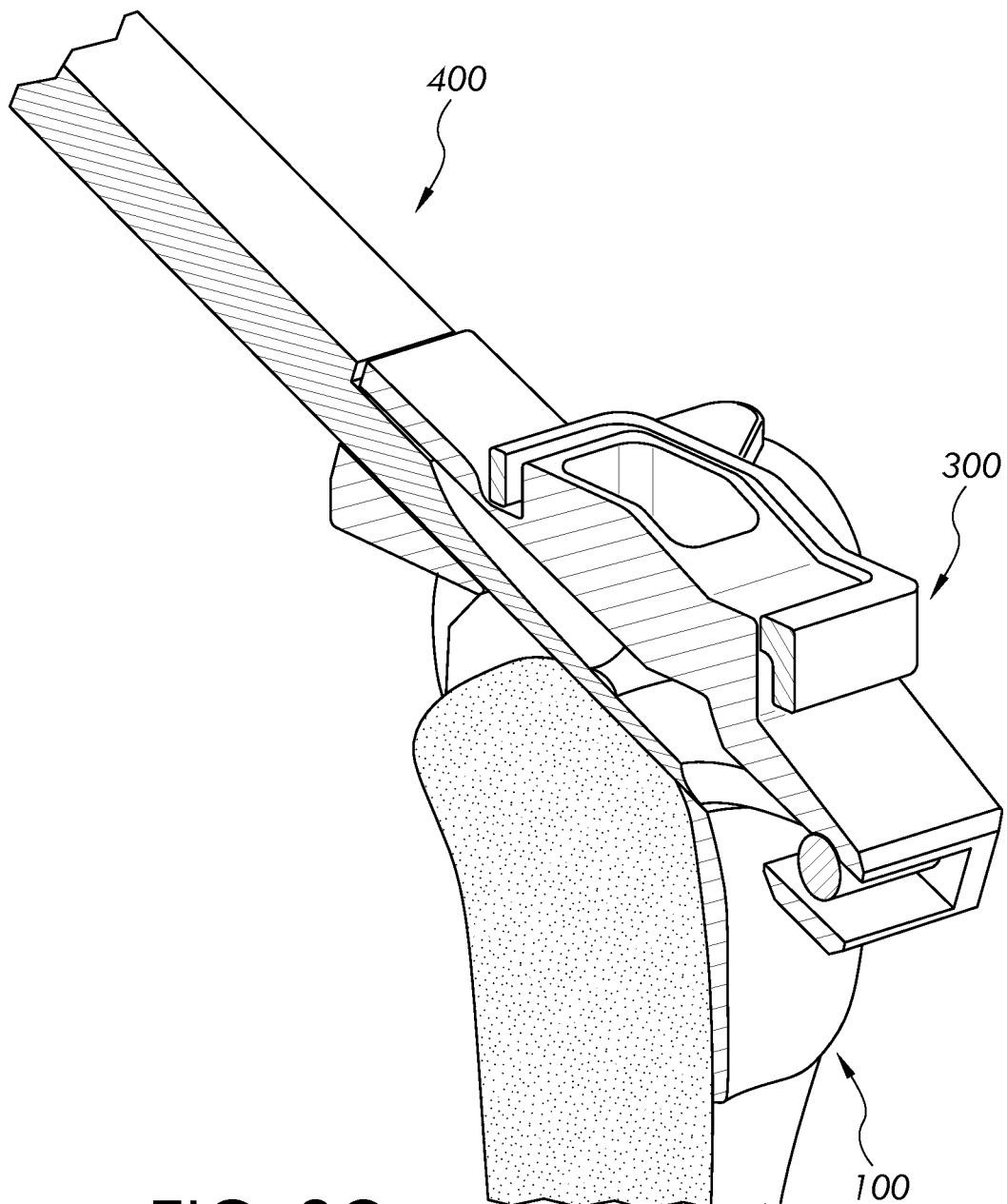
FIG. 8C is a cross sectional view of the notch preparation guide attached to the trial femoral component of FIG. 8A with a chisel.

The anterior slot 343 includes an internal feature 345 (FIG. 8B) to guide the saw 200 when the saw 200 is positioned in the anterior slot 343. The illustrated internal feature 345 has a cylindrical shape and is configured to further guide the saw 200 by restricting vertical movement of the saw 200 relative to the anterior slot 343. Moreover, the internal feature 345 is arranged to engage the chisel 400 and block or stop the chisel 400 from extending through the opening 347 when the chisel 400 is assembled with the posterior slot 330 as described in more detail below.

The anterior portion 312 also includes an opening 346 adjacent the interior edge 344, wherein the opening 346 is configured to receive a portion of the saw 200. A portion of the saw 200 may pass through the opening 347, the anterior slot 143, and the opening 346 to engage the portion of bone in the opening 106 of the femoral trial component 100 during surgery. The posterior end 342 of the anterior portion 312 includes a pair of legs 306 that may slide into grooves 130 to secure trial component 100 and notch preparation guide 300 together.

The movable arm 316 is pivotally attached to the posterior portion 314 at the hinge 318. The movable arm 316 can be spring loaded and/or lockable with the posterior portion 314 as desired during surgery. The movable arm 316 includes an anterior base member 350 opposite a posterior base member 352 and a pair of arms 354 that span between the anterior member 350 and the posterior member 352 to thereby form an opening 355. The anterior member 350, the pair of arms 354, and the posterior member 352 are arranged to receive windows 324 and the anterior end 338 of the posterior portion 314 within the opening 355. In the illustrated form, the anterior member 350, the pair of arms 354, and the posterior member 352 are arranged in a substantially rectangular shape. However, the anterior member 350, the pair of arms 354, and the posterior member 352 may be arranged in another configuration.

The movable arm 316 includes a pair of handles 356 that extend away from the pair of arms 354. While the illustrated handles 356 have a triangular shape, it is to be appreciated that the handles 356 may be shaped differently. Each of the handles 356 includes a peg 304 that extends proximally away from the handles 356 such that the peg 304 is arranged to enter into the corresponding receiving portion 128 of the femoral trial component 100 when the notch preparation guide 300 is assembled with the femoral trial component 100. The illustrated pegs 304 are cylindrical in shape and include a tapered end portion 358 configured to extend into the receiving portion 128, but may be arranged differently in another configuration.

Figure 6A:
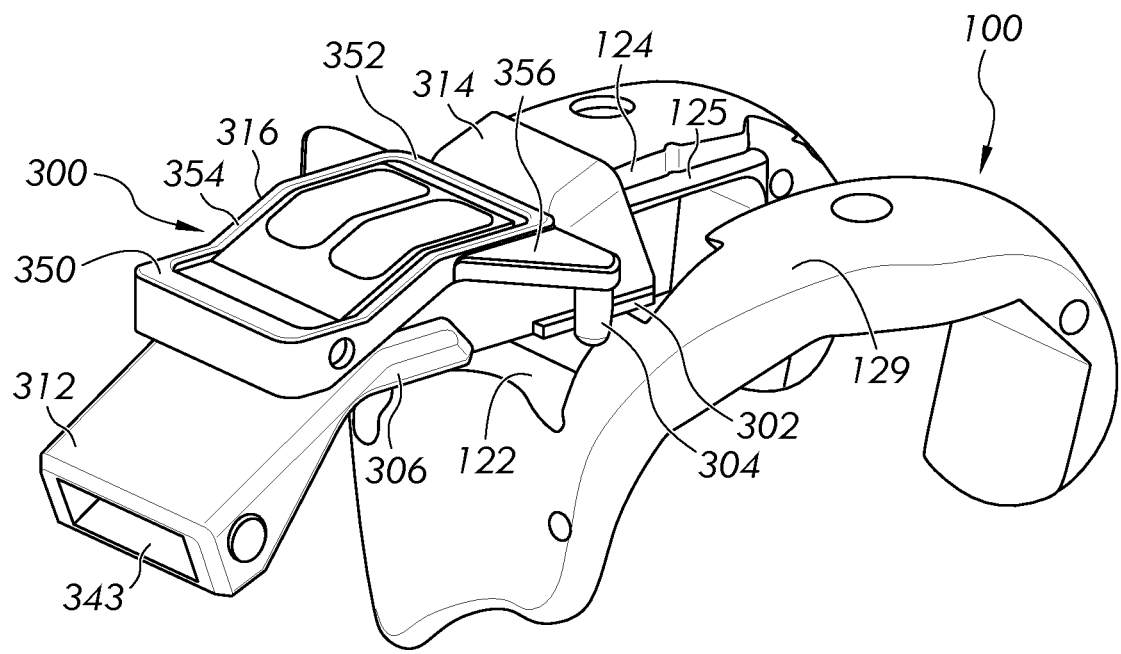
FIGS. 6A through 6C illustrate a perspective view of various states of assembly of the notch preparation guide illustrated in FIG. 2 with the trial femoral component of FIG. 5 according to one embodiment.
Figure 6B:
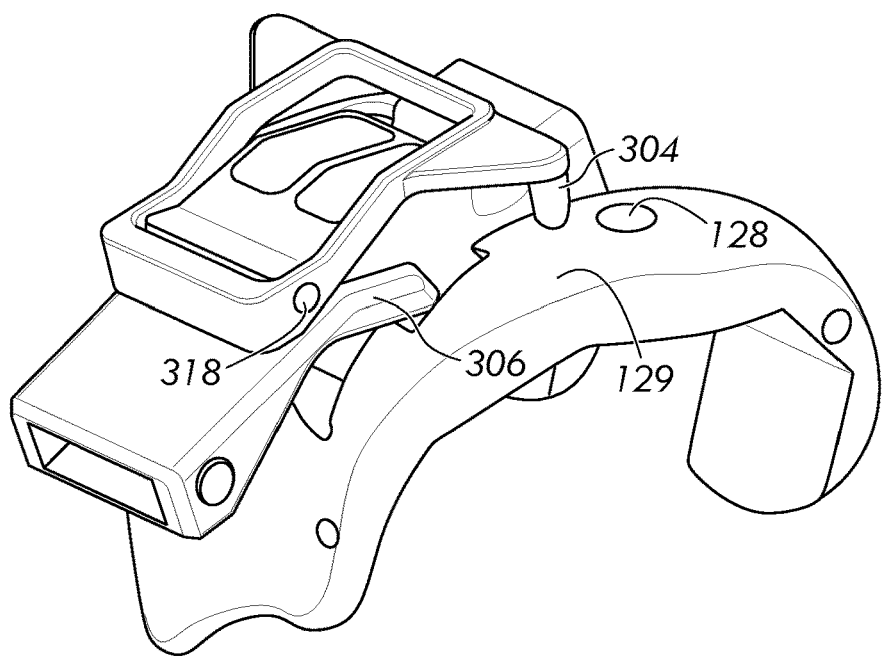
Figure 6C:
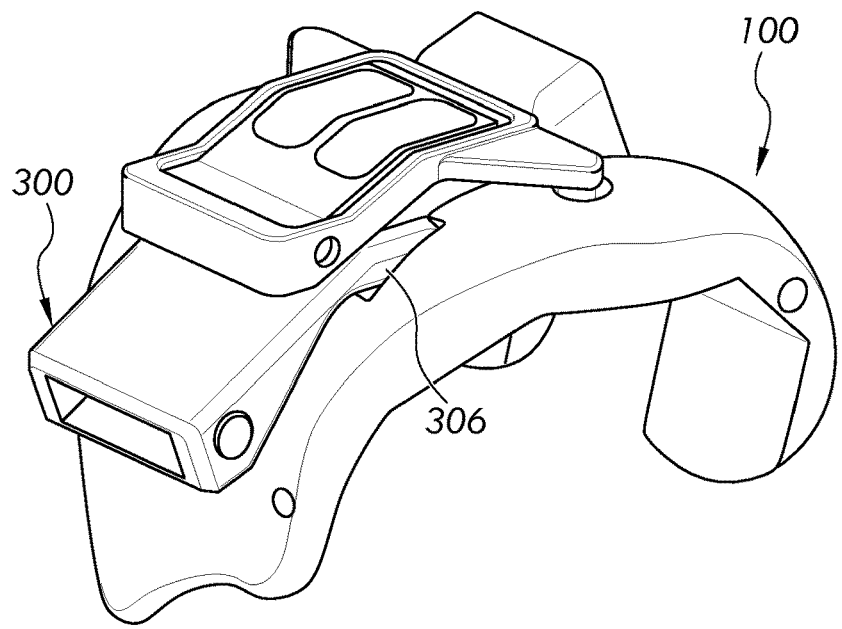
Figure 6D:
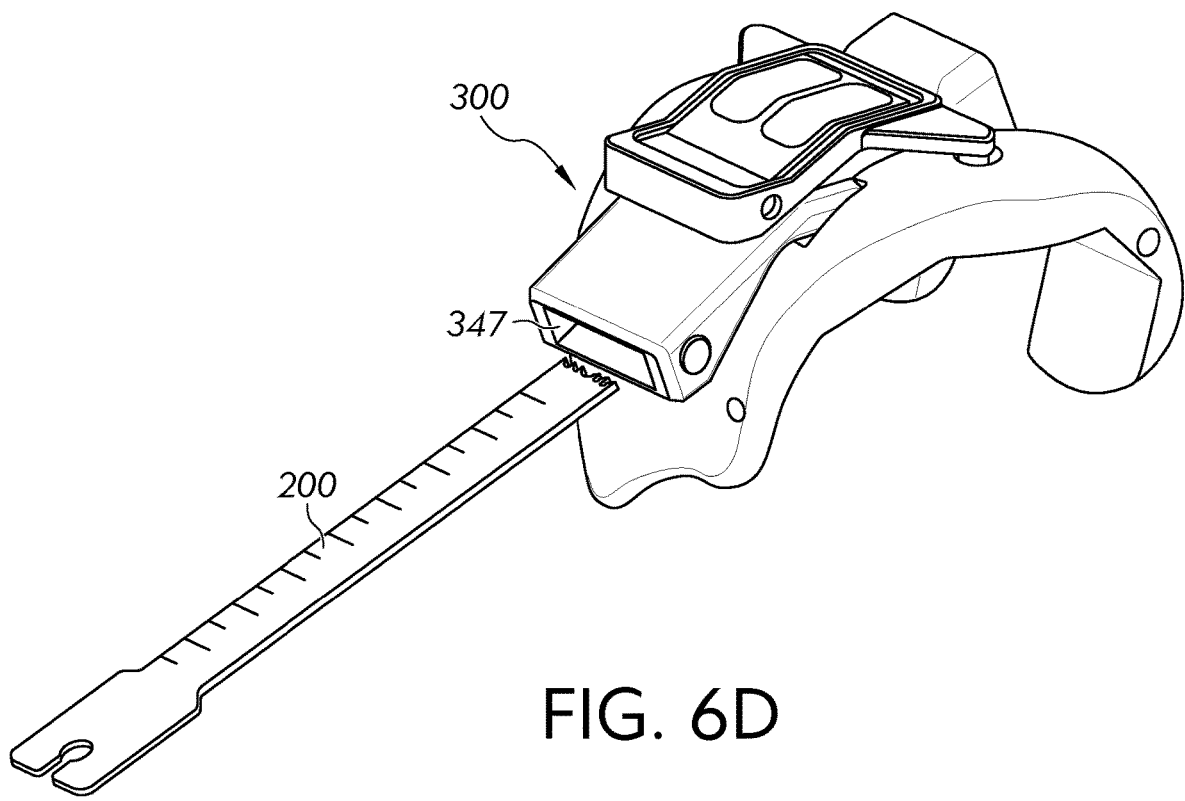
FIGS. 6D through 6E illustrate the notch preparation guide and the trial femoral component illustrated in FIGS. 6A through 6C with a saw blade.
Figure 6E:
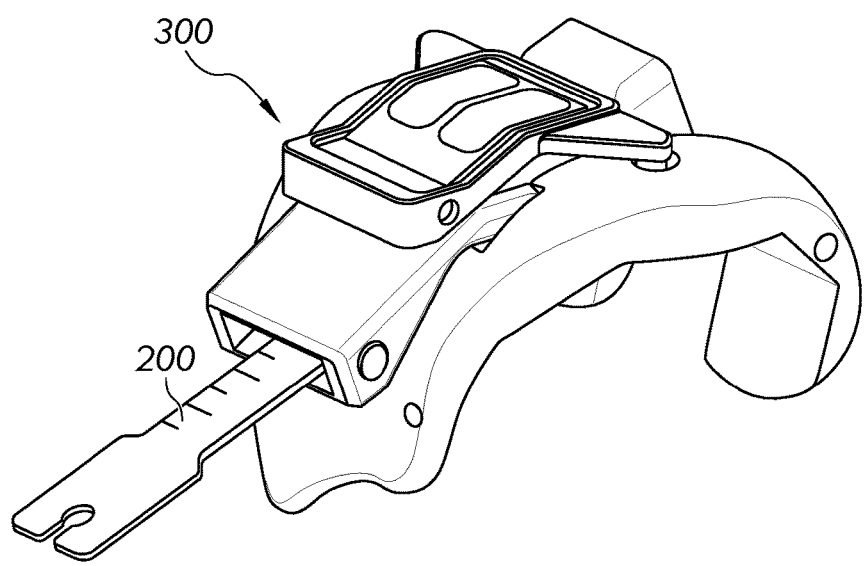
Figure 6F:
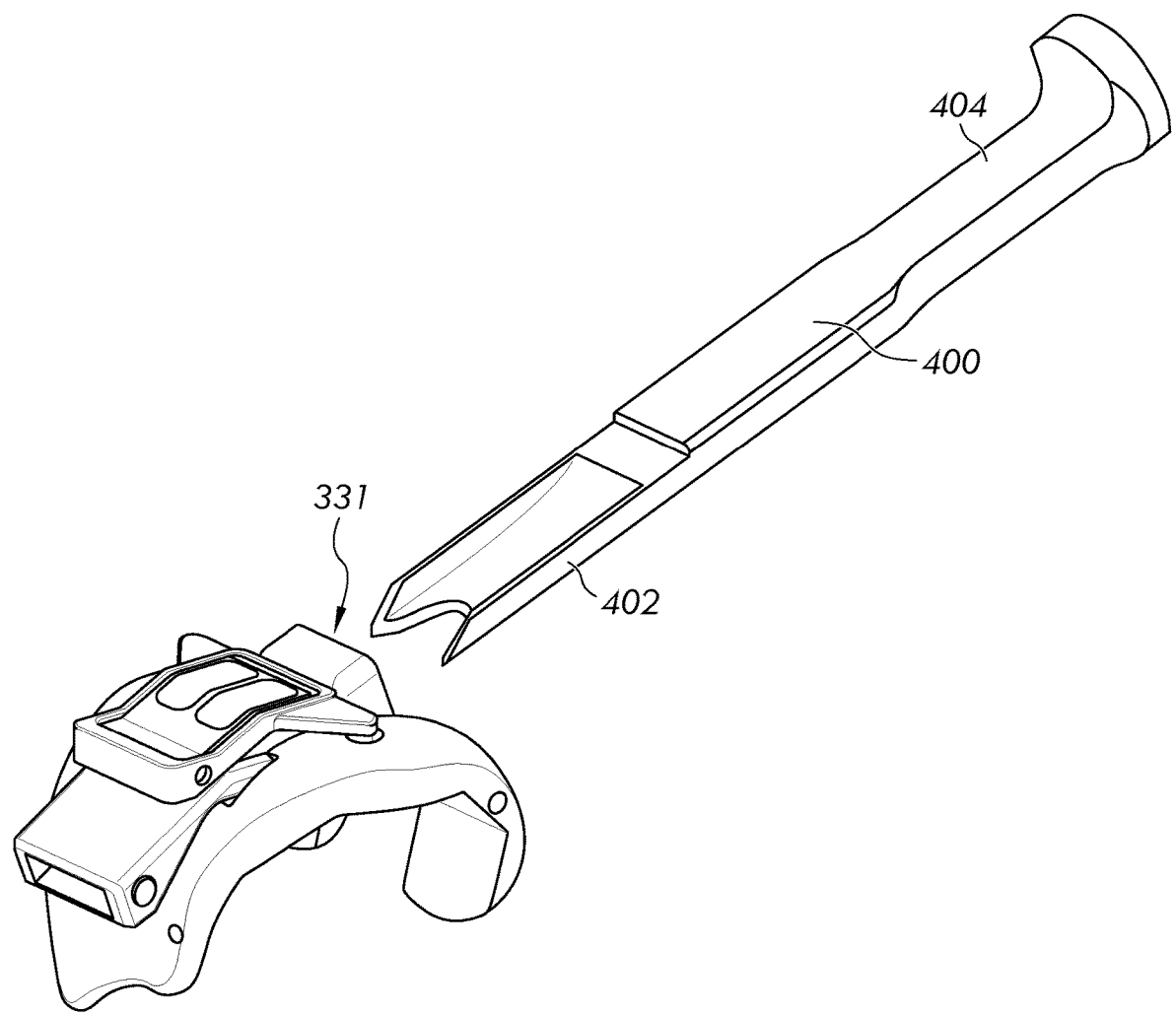
FIGS. 6F through 6H illustrate the notch preparation guide and the trial femoral component illustrated in FIGS. 6A through 6C with a chisel.
Figure 6G:
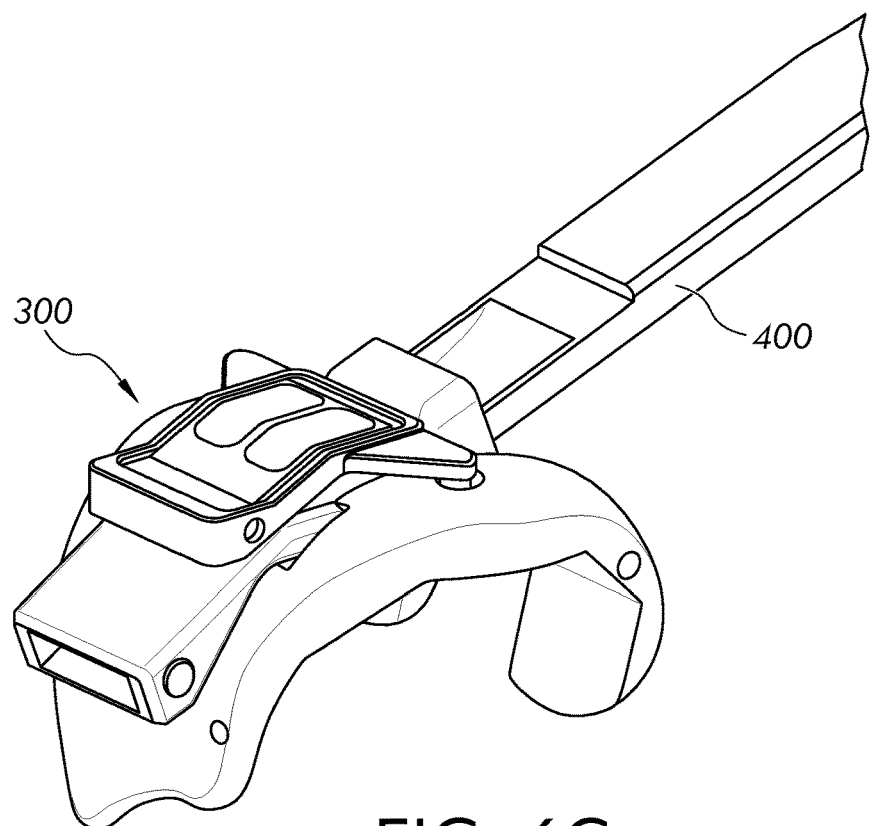
Figure 6H:
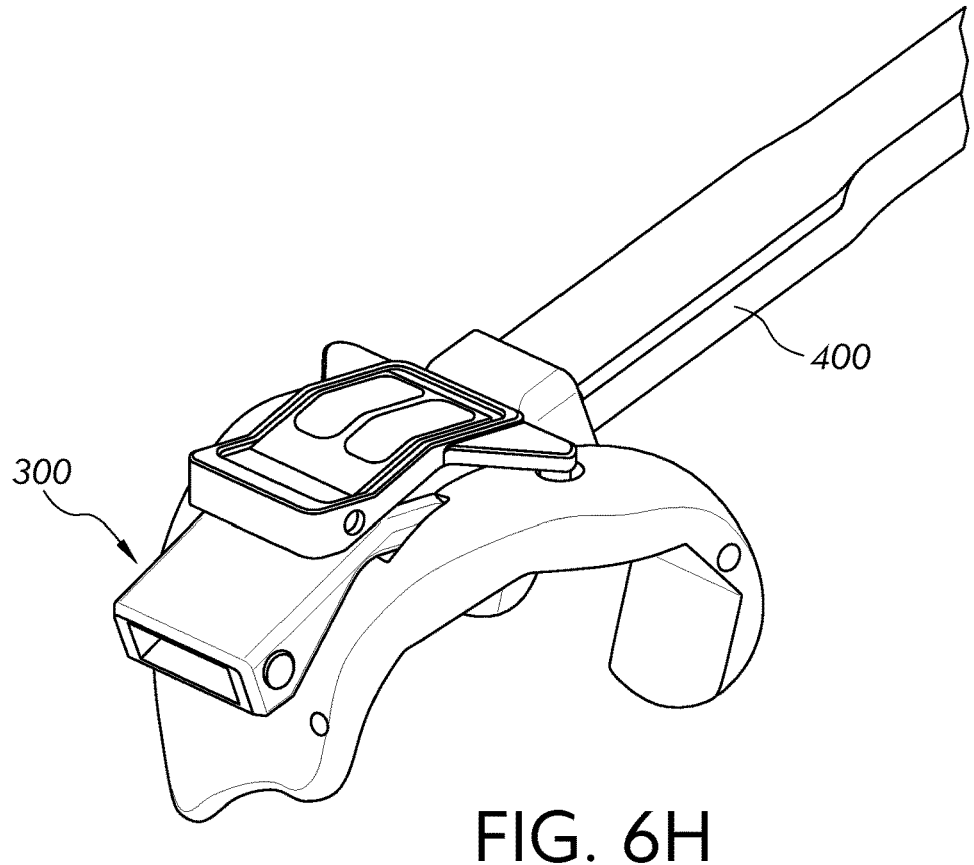

The assembly of the notch preparation guide 300 with the femoral trial component 100 will be described with reference to FIGS. 6A through 6C. The posterior portion 314 of the notch preparation guide 300 is positioned near the anterior-most portion 122 of the central portion 110 of the femoral trial component 100. The edges of outer flanges 302 of the notch preparation guide 300 slide into orientation slots 125 to secure the femoral trial component 100 and notch preparation guide 300 together. As the outer flanges 302 continue to slide in the orientation slots 125, each of the legs 306 slides into a corresponding one of the grooves 130. The grooves 130 are configured and arranged to receive the legs 306 and limit further movement of the notch preparation guide 300 relative to the femoral trial component 100 and to further secure the femoral trial component 100 and notch preparation guide 300 together.

As the notch preparation guide 300 slides relative to the femoral trial component 100, the movable arm 316 pivots about the hinge 318. Specifically, the pegs 304 rest on the distal surface 129 and slide across the distal surface 129 as the outer flanges 302 slide in the orientation slots 125. Additionally or alternatively, the movable arm 316 may be rotated about the hinge 318 by the surgeon. As the legs 306 reach the ends of the grooves 130, the pegs 304 are aligned over the receiving portions 128. The movable arm 316 may rotate about the hinge 318 and the pegs 304 enter the receiving portions 128 to secure the notch preparation guide 300 to the femoral trial component 100 as shown in FIG. 6C.

As illustrated in FIGS. 6D, 6E, 8A, and 8B, after the notch preparation guide 300 and the femoral trial component 100 are assembled, the saw blade 200 may be positioned through the opening 347, through the anterior slot 343, and through the opening 346 to engage a portion of the distal femur to enable the surgeon to form one or more precise cuts on a portion of the distal femur that is captured in the femoral trial component 100 and between the openings 346 and 336. For example, the surgeon may remove bone from the trochlear groove with the notch preparation guide 300 and saw 200. The saw 200 is also guided by the internal feature 345 to further limit the vertical movement of the saw 200 relative to the notch preparation guide 300. The anterior slot 343 is a captured guideway for the saw 200 such that the saw 200 fits within and slides relative to the anterior slot 343 to aid the surgeon in performing a precise measured cut on one or more portions of the distal femur including the trochlear groove.

In addition or as an alternative to using the saw 200 with the notch preparation guide 300, a surgeon may desire to use the chisel 400 as illustrated in FIGS. 6F-6H, 7A, 7B, and 8C. The chisel 400 may be positioned through the opening 331, the posterior slot 330, and the opening 336 such that the chisel 400 may be moved relative to the posterior slot 300. The chisel 400 may engage the portion of bone through the opening 336 after a portion of the chisel 400 travels through the posterior slot 330 to aid the surgeon in performing a precise measured cut on one or more portions of the distal femur including the trochlear groove. The chisel 400 may continue movement into the opening 346 of the anterior portion 312 into the anterior slot 343 to engage the internal feature 345 such that the internal feature 345 stops and blocks further movement of the chisel 400 through the anterior slot 343.

Figure 9:
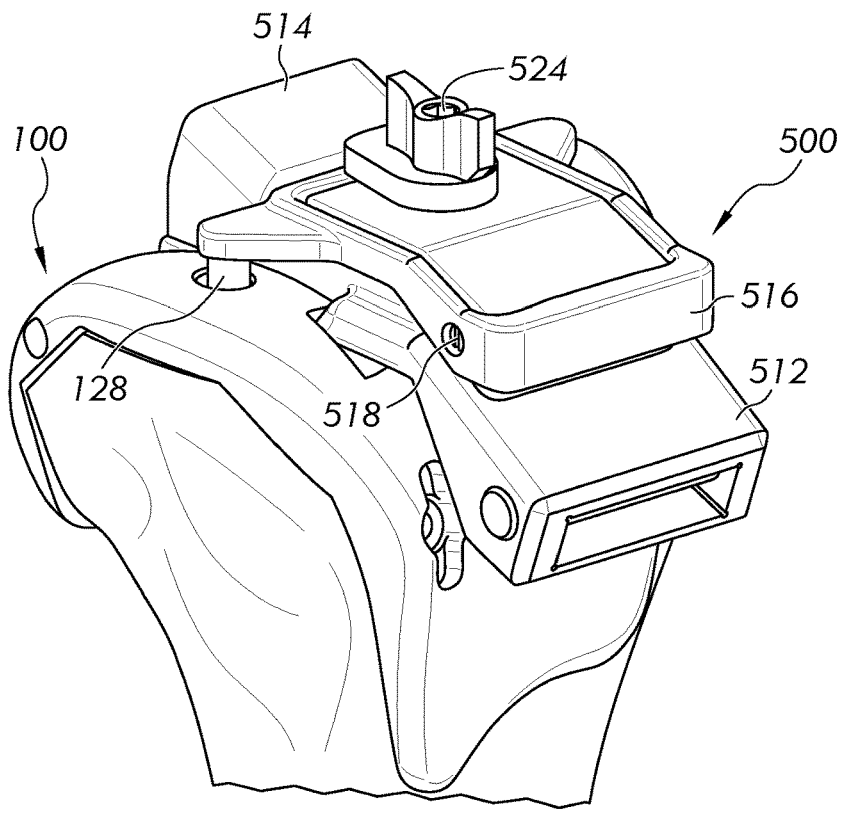
FIG. 9 is a perspective view of a notch preparation guide according to another embodiment attached to the trial femoral component of FIG. 5 implanted on a femur.
Figure 10:
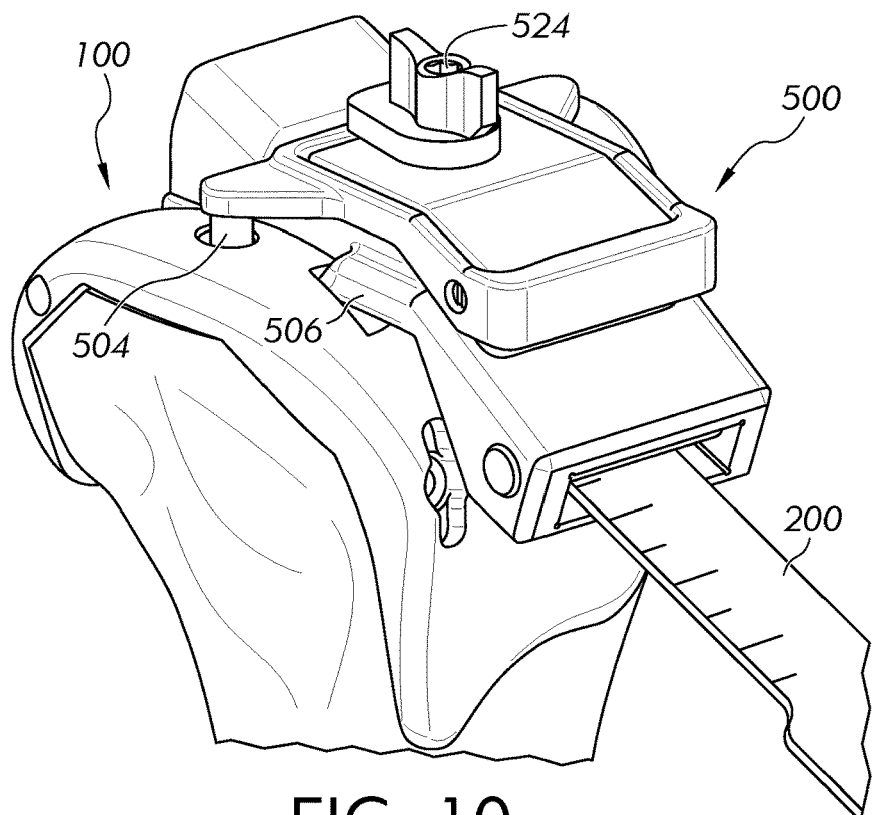
FIG. 10 is a perspective view of the notch preparation guide attached to the trial femoral component of FIG. 9 with a saw.
Figure 11:
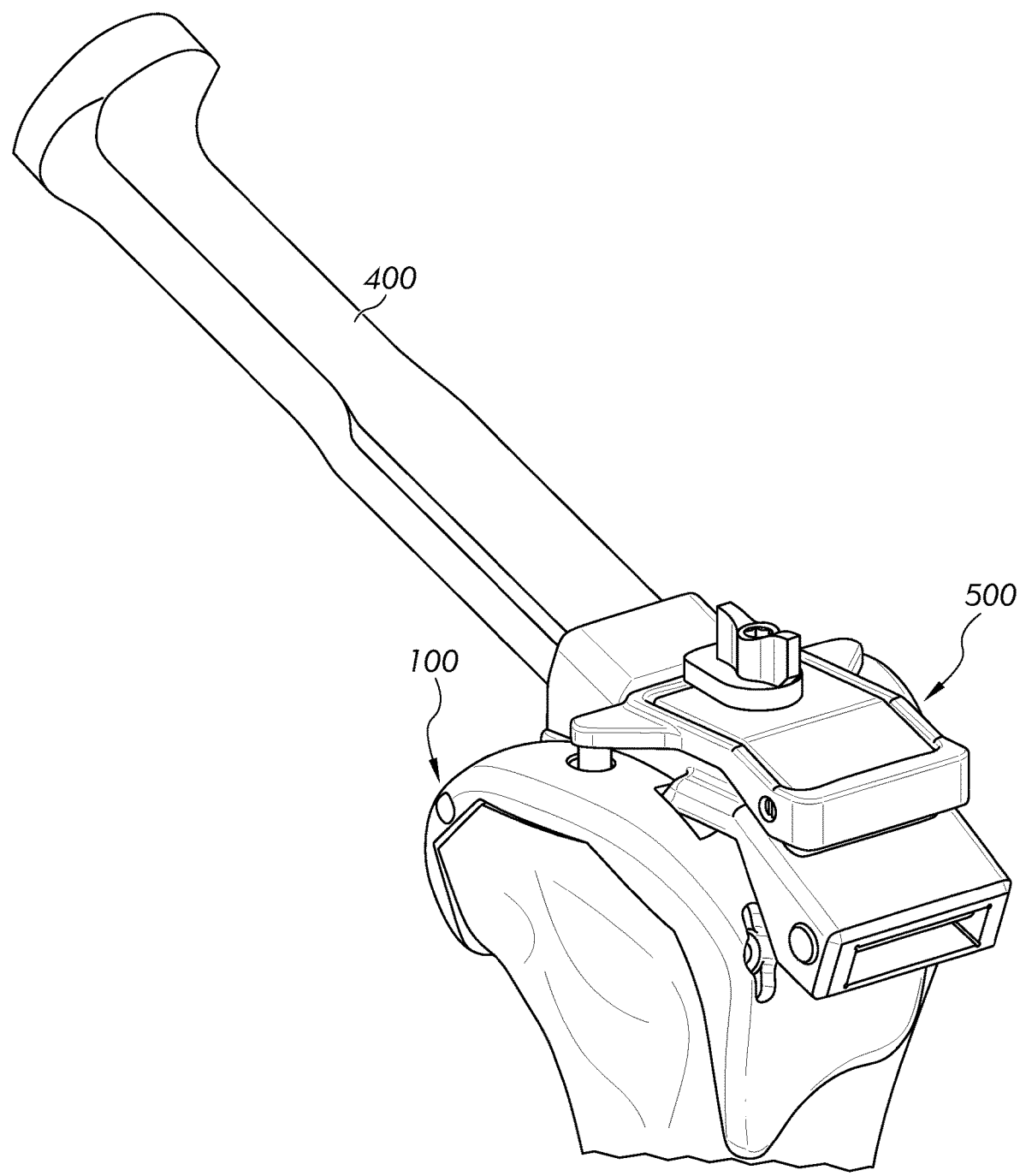
FIG. 11 is a perspective view of the notch preparation guide attached to the trial femoral component of FIG. 9 with a chisel.

FIGS. 9, 10, and 11 illustrate a notch preparation guide 500 according to another embodiment. The notch preparation guide 500 is substantially similar to the notch preparation guide 300 described above with reference to FIGS. 2-8. Unless indicated otherwise, similar reference characters are used to indicate similar elements and features. For example, the notch preparation guide 500 includes an anterior portion 512 attached to a posterior portion 514, which respectively correspond to the anterior portion 312 and the posterior portion 314. Optionally the anterior portion 512 and the posterior portion 514 can be monolithic or one-piece. The notch preparation guide 500 includes a movable arm 516 pivotally attached to the posterior portion 514 via a hinge 518. In the interest of conciseness, the following descriptions focus primarily on features that are different than those described above with regard to the notch preparation guide 300. It is to be understood, however, that the notch preparation guide 500 may include various features analogous to those described above with reference to the notch preparation guide 300, such as the distal surface 320 opposite the proximal surface 322.

The posterior portion 514 includes a locking mechanism 524 configured for operation with the movable arm 516. In an open position, the locking mechanism 524 does not restrain the movable arm 516 from movement, thereby allowing the moveable arm 516 to rotate about the hinge 518 and enable the notch preparation guide 500 to be detached from the femoral trial component 100 as desired. In a closed position, the locking mechanism 524 restrains the movable arm 516 from movement such that the moveable arm 516 cannot rotate about the hinge 518, and the notch preparation guide 500 remains securely attached to the femoral trial component 100. In one form, the locking mechanism 524 is a rotatable knob; however, the locking mechanism 524 may include other types of mechanisms operable to selectively restrain the movable arm 516 from movement.

The assembly of the notch preparation guide 500 with the femoral trial component 100 is similar to the assembly of the notch preparation guide 300 with the femoral trial component 100. The assembly of the notch preparation guide 500 with the femoral trial component 100 will be described next. The posterior portion 514 includes a pair of outer flanges similar to outer flanges 302, wherein edges of the outer flanges may slide into orientation slots 125 to secure trial component 100 and notch preparation guide 500 together.

During assembly, the posterior portion 514 of the notch preparation guide 500 is positioned near the anterior-most portion 122 of the central portion 110 of the femoral trial component 100. With the locking mechanism 524 being in an open position, the outer flanges slide along the orientation slots 125, and each of the legs 506 slides into a corresponding one of the grooves 130. The grooves 130 are configured and arranged to receive the legs 506 and limit further movement of the notch preparation guide 500 relative to the femoral trial component 100, and to further secure the femoral trial component 100 and notch preparation guide 500 together. While the notch preparation guide 500 slides relative to the femoral trial component 100, the movable arm 516 pivots about the hinge 518. Specifically, the pegs 504 rest on the distal surface 129 and slide across the distal surface 129 as the outer flanges slide in the orientation slots 125. Additionally or in the alternative, the movable arm 516 may be rotated about the hinge 518 by the surgeon.

As the legs 506 reach the ends of the grooves 130, the pegs 504 are aligned over the receiving portions 128. The movable arm 516 may rotate about the hinge 518 such that the pegs 504 enter the receiving portions 128 to secure the notch preparation guide 500 to the femoral trial component 100 as shown in FIGS. 9, 10, and 11. The locking mechanism 524 is moved from an open position to a closed position to restrain the movable arm 516 from movement and further lock the notch preparation guide 500 on the femoral trial component 100. When it is desired to remove the notch preparation guide 500 from the femoral trial component 100, the locking mechanism 524 is moved from a closed position to an open position to enable movement of the movable arm 516 about the hinge 518.

Figure 12:
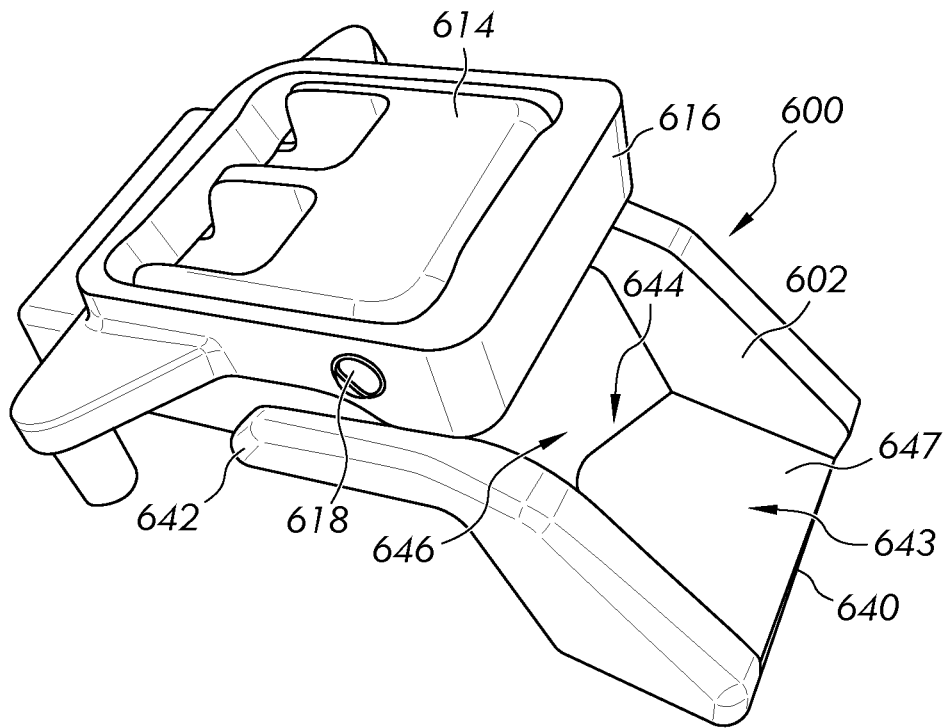
FIG. 12 is a perspective view of a notch preparation guide according to another embodiment with an extended saw guide platform.
Figure 13:
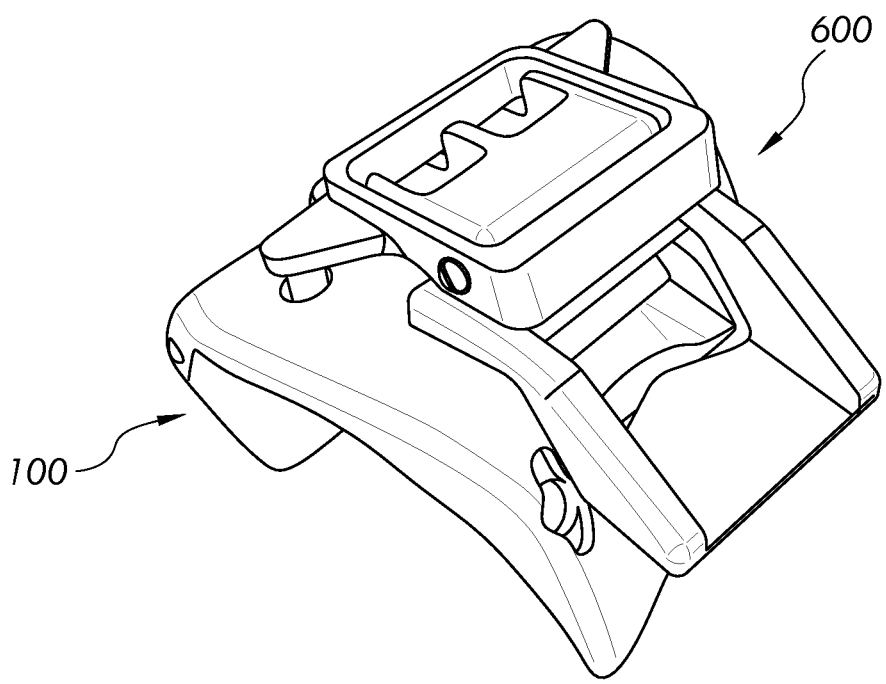
FIG. 13 is a perspective view of the notch preparation guide illustrated in FIG. 12 attached to a trial femoral component.

FIGS. 12 and 13 illustrate a notch preparation guide 600 according to another embodiment, which includes an extended uncaptured saw guide platform. The notch preparation guide 600 is substantially similar to the notch preparation guide 300 described above with reference to FIGS. 2-8. Unless indicated otherwise, similar reference characters are used to indicate similar elements and features. For example, the notch preparation guide 600 includes an anterior portion 602 attached to a posterior portion 614. The anterior portion 602 is different than the anterior portion 312 and is described below. The notch preparation guide 600 includes a movable arm 616 pivotally attached 618 to the posterior portion 614. In the interest of conciseness, the following descriptions focus primarily on features that are different than those described above with regard to the notch preparation guide 300. It is to be understood, however, that the notch preparation guide 600 may include various features analogous to those described above with reference to the notch preparation guide 300, such as the distal surface 320 opposite the proximal surface 322.

The anterior portion 602 spans between an anterior end 640 and a posterior end 642. The anterior portion 602 includes an anterior slot 643 sized to receive the saw 200, wherein the anterior slot 643 spans from an opening 647 at the anterior end 640 to an opening 646 at an interior edge 644. The anterior slot 643 is a guideway for the saw 200 such that the saw 200 rests against the anterior slot 643 and slides relative to the anterior slot 643.

The anterior portion 612 also includes an opening 646 adjacent the interior edge 644. The opening 646 is configured to receive a portion of bone from the patient and the saw 200. A portion of the saw 200 may pass through the opening 647, rest against the anterior slot 643, and pass through the opening 646 to engage the portion of bone in the opening 106 of the femoral trial component 100 during surgery.

The posterior portion 614 is a latch that may pivot about the hinge 618, and in the illustrated form is not configured to receive a chisel 400. The notch preparation guide 600 is assembled with the femoral trial 100 similarly as the notch preparation guide 300 is assembled with the femoral trial 100.

Any of the notch preparation guides can be assembled as a set and packaged with the first cutting instrument and/or the second cutting instrument as a medical kit. In one embodiment, there are four notch preparation guides, wherein each of the notch preparation guides is a different size, packaged with the either the first cutting instrument and/or the second cutting instrument. Any of the notch preparation guides may be used with either right or left knees.

There is provided a notch preparation guide for engagement with a femoral trial component, the notch preparation guide comprising: an anterior portion having an anterior slot arranged to receive a portion of a first cutting instrument therein; a posterior portion having a posterior slot arranged to receive a portion of a second cutting instrument therein; wherein the anterior slot and the posterior slot are arranged to capture a portion of a distal femur therebetween for removal by either of the first cutting instrument or the second cutting instrument.

In certain embodiments, the anterior portion has a first opening at an end of the anterior slot, and wherein the first opening is adapted to receive either the portion of the first cutting instrument or the portion of the second cutting instrument.

In certain embodiments, the anterior portion includes a second opening at an opposite end of the anterior slot, the second opening configured to receive the portion of the first cutting instrument, the anterior slot further arranged such that the first cutting instrument can move from an anterior direction to a posterior direction in the anterior slot.

In certain embodiments, the anterior slot includes an internal feature arranged to guide the portion of the first cutting instrument positioned in the anterior slot.

In certain embodiments, the internal feature has a cylindrical shape and is arranged to restrict vertical movement of the first instrument relative to the anterior slot.

In certain embodiments, the internal feature is arranged to stop movement of the portion of the second cutting instrument through the second opening of the anterior portion when the second cutting instrument is assembled with the posterior slot.

In certain embodiments, the anterior slot is positioned and aligned opposite of the posterior slot to enable movement of the portion of the first cutting instrument through the anterior slot and into the posterior slot.

In certain embodiments, the anterior slot is positioned and aligned opposite of the posterior slot to enable movement of the portion of the second cutting instrument through the posterior slot and into the anterior slot.

In certain embodiments, the posterior portion includes a first opening at an end of the posterior slot, the first opening is adapted to receive the portion of the second cutting instrument.

In certain embodiments, the notch preparation guide further comprises a pair of flanges configured to slide into a pair of orientation slots formed in the femoral trial component.

In certain embodiments, at least one of the anterior slot or the posterior slot forms a captured guideway.

In certain embodiments, at least one of the anterior slot or the posterior slot is substantially rectangular in cross-sectional shape.

In certain embodiments, the first cutting instrument is a saw, and wherein the second cutting instrument is a chisel.

In certain embodiments, the posterior portion includes one or more windows extending between a distal surface of the posterior portion and a proximal surface of the posterior portion.

In certain embodiments, the notch preparation guide further comprises a lock adapted to move between an open position in which the notch preparation guide is detachable from the femoral trial component and a closed position in which the notch preparation guide is fixedly attached to the femoral trial component.

In certain embodiments, the notch preparation guide further comprises a movable arm pivotally attached to the posterior portion, the moveable arm adapted to move between an open position in which the notch preparation guide is detachable from the femoral trial component and a closed position in which the notch preparation guide is attached to the femoral trial component.

In certain embodiments, the notch preparation guide further comprises a locking mechanism operable to selectively retain the movable arm in the closed position.

In certain embodiments, the movable arm is biased toward the closed position.

In certain embodiments, the movable arm further includes a post operable to be received in a recess of the femoral trial component when the movable arm is in the closed position.

In certain embodiments, the portion of the distal femur comprises a trochlear groove.

There is also provided a method of knee arthroplasty, the method comprising: resecting a patient's distal femur with anterior and posterior cuts; positioning a femoral trial component on the distal femur, the femoral trial component having an opening provided between a first condylar component and a second condylar component; attaching a notch preparation guide in the opening of the femoral trial component, the notch preparation guide having an anterior portion that defines an anterior slot arranged to receive a portion of a first cutting instrument therein, the notch preparation guide having a posterior portion that defines a posterior slot arranged to receive a portion of a second cutting instrument therein; and preparing the patient's distal femur using either the anterior slot to guide the first cutting instrument or the posterior slot to guide the second cutting instrument.

In certain embodiments, the anterior slot and the posterior slot are arranged to capture a portion of a distal femur therebetween for removal by either the first cutting instrument or the second cutting instrument.

In certain embodiments, the method further comprises moving the portion of the first cutting instrument in the anterior slot from an anterior direction to a posterior direction.

In certain embodiments, the moving includes oscillating and the first cutting instrument is a saw.

In certain embodiments, the method further comprises moving the portion of the first cutting instrument through the anterior slot and into the posterior slot.

In certain embodiments, the method further comprises moving the portion of the second cutting instrument in the posterior slot from a posterior direction to an anterior direction.

In certain embodiments, the second cutting instrument is a chisel.

In certain embodiments, the method further comprises moving the portion of the second cutting instrument through the posterior slot and into the anterior slot.

In certain embodiments, the method further comprises engaging the portion of the second cutting instrument with an internal feature arranged in the anterior slot to stop movement of the portion of the second cutting instrument through a second opening of the anterior portion.

In certain embodiments, the preparing includes removing at least a portion of a trochlear groove of the distal femur using at least one of the first cutting instrument or the second cutting instrument.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A notch preparation guide for engagement with a femoral trial component, the notch preparation guide comprising:
   an anterior portion having an anterior slot arranged to receive a portion of a first cutting instrument therein;
   a posterior portion having a posterior slot arranged to receive a portion of a second cutting instrument therein; and
   a movable arm pivotally attached to the posterior portion, the moveable arm adapted to move between an open position in which the notch preparation guide is detachable from the femoral trial component and a closed position in which the notch preparation guide is attached to the femoral trial component;
   wherein the anterior slot and the posterior slot are arranged to capture a portion of a distal femur therebetween for removal by either of the first cutting instrument or the second cutting instrument.

2. The notch preparation guide of claim 1, wherein the anterior portion has a first opening at an end of the anterior slot, and wherein the first opening is adapted to receive either the portion of the first cutting instrument or the portion of the second cutting instrument.

3. The notch preparation guide of claim 2, wherein the anterior portion includes a second opening at an opposite end of the anterior slot, the second opening configured to receive the portion of the first cutting instrument, the anterior slot further arranged such that the first cutting instrument can move from an anterior direction to a posterior direction in the anterior slot.

4. The notch preparation guide of claim 3, wherein the anterior slot includes an internal feature arranged to guide the portion of the first cutting instrument positioned in the anterior slot.

5. The notch preparation guide of claim 4, wherein the internal feature has a cylindrical shape and is arranged to restrict vertical movement of the first instrument relative to the anterior slot.

6. The notch preparation guide of claim 4, wherein the internal feature is arranged to stop movement of the portion of the second cutting instrument through the second opening of the anterior portion when the second cutting instrument is assembled with the posterior slot.

7. The notch preparation guide of claim 1, wherein the anterior slot is positioned and aligned opposite of the posterior slot to enable movement of the portion of the first cutting instrument through the anterior slot and into the posterior slot.

8. The notch preparation guide of claim 1, wherein the anterior slot is positioned and aligned opposite of the posterior slot to enable movement of the portion of the second cutting instrument through the posterior slot and into the anterior slot.

9. The notch preparation guide of claim 1, wherein the posterior portion includes a first opening at an end of the posterior slot, the first opening is adapted to receive the portion of the second cutting instrument.

10. The notch preparation guide of claim 1, further comprising a pair of flanges configured to slide into a pair of orientation slots formed in the femoral trial component.

11. The notch preparation guide of claim 1, wherein at least one of the anterior slot or the posterior slot forms a captured guideway.

12. The notch preparation guide of claim 1, wherein at least one of the anterior slot or the posterior slot is substantially rectangular in cross-sectional shape.

13. The notch preparation guide of claim 1, wherein the first cutting instrument is a saw, and wherein the second cutting instrument is a chisel.

14. The notch preparation guide of claim 1, wherein the posterior portion includes one or more windows extending between a distal surface of the posterior portion and a proximal surface of the posterior portion.

15. The notch preparation guide of claim 1, further comprising a locking mechanism operable to selectively retain the movable arm in the closed position.

16. The notch preparation guide of claim 1, wherein the movable arm is biased toward the closed position.

17. The notch preparation guide of claim 1, wherein the movable arm further includes a post operable to be received in a recess of the femoral trial component when the movable arm is in the closed position.

18. The notch preparation guide of claim 1, wherein the portion of the distal femur comprises a trochlear groove.

19. A method of knee arthroplasty, comprising:
resecting a patient's distal femur with anterior and posterior cuts; positioning a femoral trial component on the distal femur, the femoral trial component having an opening provided between a first condylar component and a second condylar component;
attaching a notch preparation guide in the opening of the femoral trial component, the notch preparation guide having an anterior portion that defines an anterior slot arranged to receive a portion of a first cutting instrument therein, the notch preparation guide having a posterior portion that defines a posterior slot arranged to receive a portion of a second cutting instrument therein; and
preparing the patient's distal femur using either the anterior slot to guide the first cutting instrument or the posterior slot to guide the second cutting instrument.

20. The method of claim 19, wherein the anterior slot and the posterior slot are arranged to capture a portion of a distal femur there between for removal by either the first cutting instrument or the second cutting instrument.

21. The method of claim 19, further comprising:
moving the portion of the first cutting instrument in the anterior slot from an anterior direction to a posterior direction.

22. The method of claim 21, wherein the moving includes oscillating and the first cutting instrument is a saw.

23. The method of claim 21, further comprising:
moving the portion of the first cutting instrument through the anterior slot and into the posterior slot.

24. The method of claim 23, further comprising:
moving the portion of the second cutting instrument in the posterior slot from a posterior direction to an anterior direction.

25. The method of claim 23, wherein the second cutting instrument is a chisel.

26. The method of claim 23, further comprising:
moving the portion of the second cutting instrument through the posterior slot and into the anterior slot.

27. The method of claim 26, further comprising:
engaging the portion of the second cutting instrument with an internal feature arranged in the anterior slot to stop movement of the portion of the second cutting instrument through a second opening of the anterior portion.

28. The method of claim 19, wherein the preparing includes removing at least a portion of a trochlear groove of the distal femur using at least one of the first cutting instrument or the second cutting instrument.

29. A notch preparation guide for engagement with a femoral trial component, the notch preparation guide comprising:
an anterior portion having an anterior slot arranged to receive a portion of a first cutting instrument therein; and
a posterior portion having a posterior slot arranged to receive a portion of a second cutting instrument therein;
wherein:
the anterior slot and the posterior slot are arranged to capture a portion of a distal femur therebetween for removal by either of the first cutting instrument or the second cutting instrument;
the anterior portion includes a first opening at an end of the anterior slot, a second opening at an opposite end of the anterior slot, and an internal feature arranged to guide the portion of the first cutting instrument positioned in the anterior slot, the first opening is adapted to receive either the portion of the first cutting instrument or the portion of the second cutting instrument;

the second opening is configured to receive the portion of the first cutting instrument, the anterior slot further arranged such that the first cutting instrument can move from an anterior direction to a posterior direction in the anterior slot; and the internal feature is arranged to stop movement of the portion of the second cutting instrument through the second opening of the anterior portion when the second cutting instrument is assembled with the posterior slot.

\* \* \* \* \*